US008602999B2

United States Patent
Young et al.

(10) Patent No.: US 8,602,999 B2
(45) Date of Patent: Dec. 10, 2013

(54) IMPLANTABLE FLAT BLOOD PRESSURE SENSING CUFF STRUCTURE AND IMPLANTABLE BLOOD PRESSURE MONITORING DEVICE USING THE CUFF STRUCTURE

(76) Inventors: Darrin J. Young, Salt Lake City, UT (US); Wen H. Ko, Cleveland Heights, OH (US)

(*) Notice: Subject to any disclaimer, the term of this patent is extended or adjusted under 35 U.S.C. 154(b) by 345 days.

(21) Appl. No.: 12/884,037

(22) Filed: Sep. 16, 2010

(65) Prior Publication Data

US 2011/0066046 A1  Mar. 17, 2011

Related U.S. Application Data

(60) Provisional application No. 61/242,835, filed on Sep. 16, 2009.

(51) Int. Cl.
*A61B 5/02* (2006.01)
(52) U.S. Cl.
USPC .......................................................... 600/486
(58) Field of Classification Search
USPC .......................................... 600/334, 335, 486
See application file for complete search history.

(56) References Cited

U.S. PATENT DOCUMENTS

| | | | | |
|---|---|---|---|---|
| 5,722,414 A * | 3/1998 | Archibald et al. | | 600/485 |
| 2003/0097073 A1* | 5/2003 | Bullister et al. | | 600/486 |
| 2004/0152999 A1* | 8/2004 | Cohen et al. | | 600/561 |
| 2006/0047205 A1* | 3/2006 | Ludomirsky et al. | | 600/486 |
| 2006/0287569 A1* | 12/2006 | Schock et al. | | 600/18 |
| 2008/0021336 A1* | 1/2008 | Dobak, III | | 600/508 |

* cited by examiner

*Primary Examiner* — Navin Natnithithadha
*Assistant Examiner* — Etsub Berhanu
(74) *Attorney, Agent, or Firm* — Thomas H. Ham; Wilson Ham & Holman (57) ABSTRACT

An implantable flat blood pressure sensing cuff structure and an implantable blood pressure monitoring device use a first portion of the cuff structure that comprises a sidewall that extends from a surface and contains a pressure sensor, and a second portion of the cuff structure that is configured to overlie and be removably relative to the first portion. The first and second portions of the cuff structure are configured to provide an aperture extending transversely through the cuff structure for receiving a blood vessel therein generally sandwiched between the first portion and the second portion when the second portion is positioned on the first portion such that the pressure sensor is operative to detect vessel expansion and contraction.

20 Claims, 9 Drawing Sheets

IMPLANTABLE FLAT BLOOD PRESSURE SENSING CUFF STRUCTURE AND IMPLANTABLE BLOOD PRESSURE MONITORING DEVICE USING THE CUFF STRUCTURE

CROSS REFERENCE TO RELATED APPLICATION

This application is entitled to the benefit of U.S. Provisional Patent Application Ser. No. 61/242,835, filed on Sep. 16, 2009, which is incorporated herein by reference.

GOVERNMENT RIGHTS

The invention described herein was made with proceeds from National Science Foundation Grant No. EIA-0329811. The Government has certain rights in the invention.

FIELD OF THE INVENTION

The invention relates to monitoring devices, and more particularly to an implantable blood monitoring device.

BACKGROUND OF THE INVENTION

A variety of animals are used for biomedical research. As but one example, genetically engineered mice may be considered one of the most important animal models for advanced biomedical research because these mice share a high degree of homology to humans with completely sequenced genetic information. Furthermore, mice can be reproduced quickly, which is crucial for system biology research, where several generations of mice are typically required to obtain the desirable strains with targeted genetic sequences.

However, the small blood vessel size of mice, approximately 200 μm in diameter for major arteries, introduces significant challenges for in vivo blood pressure monitoring on free roaming animals. It is difficult to apply many previously developed types of blood pressure sensing cuffs in mice for in vivo real-time monitoring. Furthermore, complexities often arise due to significantly increased complexity in fabrication, packaging, and implant procedure.

In view of these concerns, there is a need for an implantable blood monitoring device for effective in vivo real-time monitoring.

SUMMARY OF THE INVENTION

An implantable flat blood pressure sensing cuff structure in accordance with an embodiment of the invention comprises a first portion that comprises a sidewall that extends from a surface and contains a pressure sensor and a second portion that is configured to overlie and be removably relative to the first portion. The first and second portions are configured to provide an aperture extending transversely through the cuff structure for receiving a blood vessel therein generally sandwiched between the first portion and the second portion when the second portion is positioned on the first portion such that the pressure sensor is operative to detect vessel expansion and contraction.

An implantable blood pressure monitoring device in accordance with an embodiment of the invention comprises a substrate and a flat blood pressure sensing cuff structure situated on the substrate. The cuff structure comprises a first portion that comprises a sidewall that extends from a surface and contains a pressure sensor, and a second portion that is configured to overlie and be removably relative to the first portion. The first and second portions are configured to provide an aperture extending transversely through the cuff structure for receiving a blood vessel therein generally sandwiched between the first portion and the second portion when the second portion is positioned on the first portion such that the pressure sensor is operative to detect vessel expansion and contraction.

Other aspects and/or advantages of the present invention will become apparent from the following detailed description, taken in conjunction with the accompanying drawings, illustrated by way of example of the principles of the invention.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment. Rather, language referring to the features and advantages is understood to mean that a specific feature, advantage, or characteristic described in connection with an embodiment is included in at least one embodiment. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment. Thus, the phrases "in one embodiment," "in an embodiment," and similar language throughout this specification may, but do not necessarily, all refer to the same embodiment.

Figure 1:
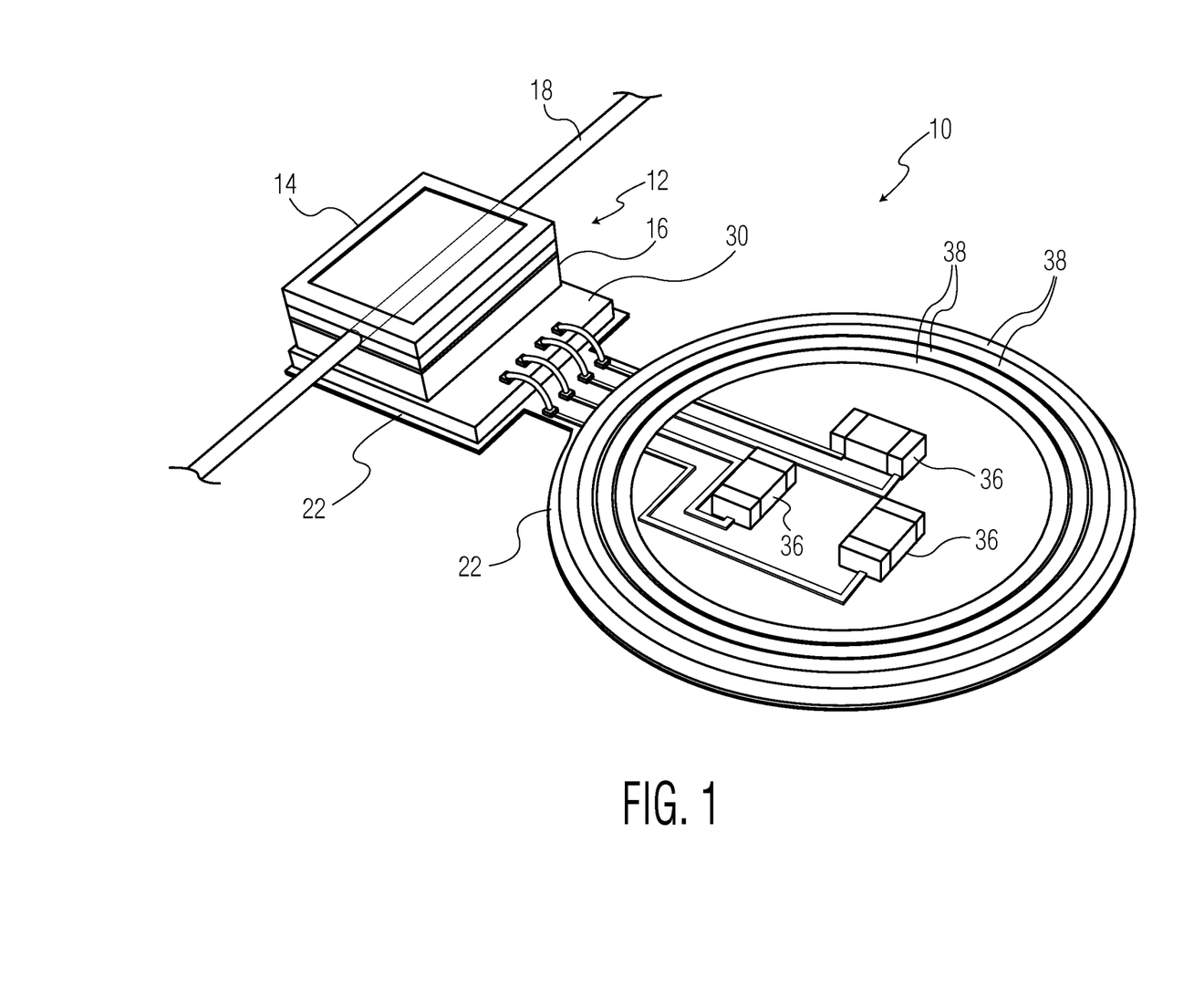
FIG. 1 is a perspective view of an implantable blood pressure monitoring device in accordance with an embodiment of the invention.
Figure 2:
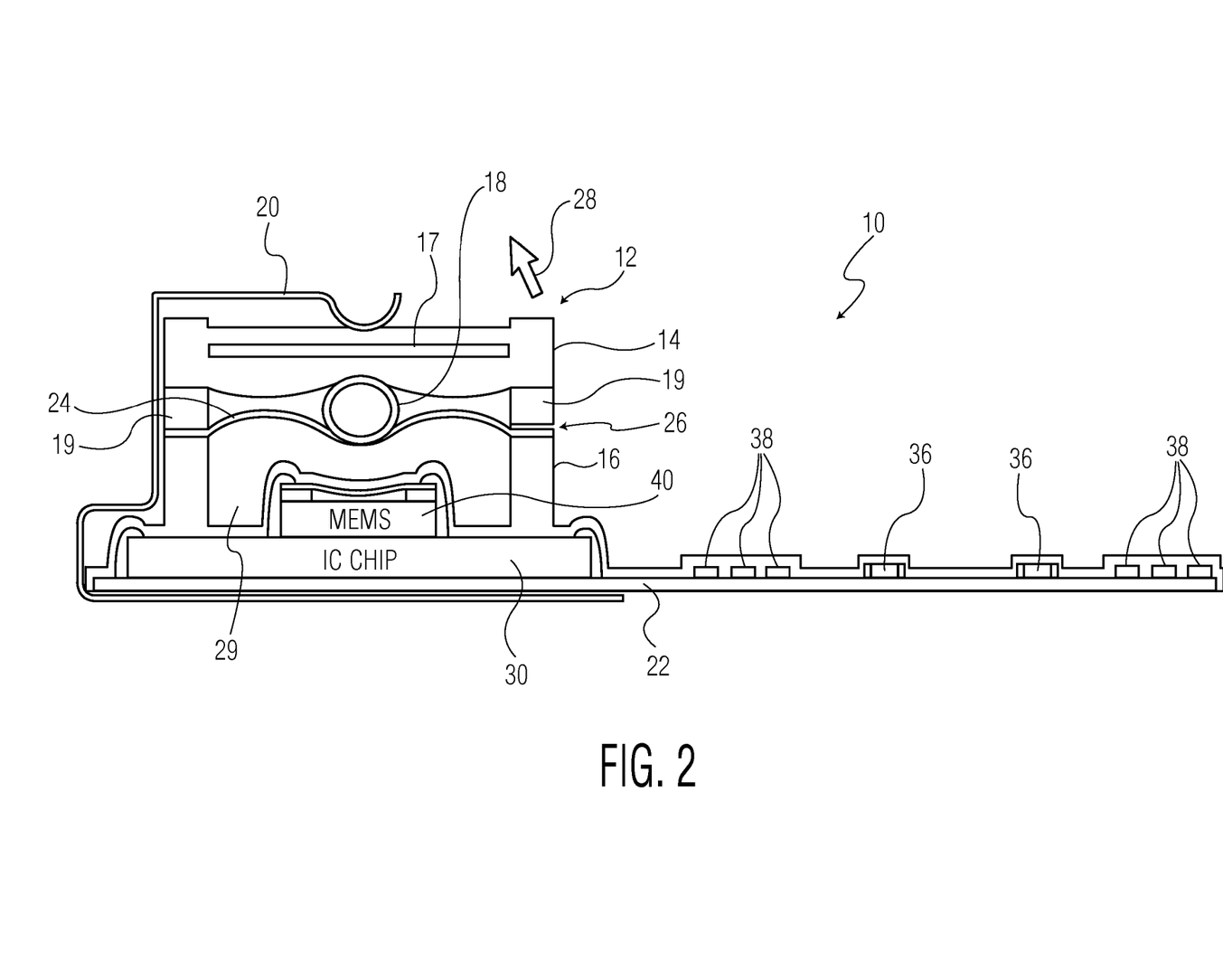
FIG. 2 is a cross-sectional view of the implantable blood pressure monitoring device.

FIGS. 1 and 2 depict an example of an implantable blood pressure monitoring device 10 in accordance with an embodiment of the invention. FIG. 1 depicts a perspective view of the device and FIG. 2 depicts a cross sectional view. The device 10 includes a substantially flat implantable blood pressure sensing cuff structure 12 that can be utilized for in vivo blood pressure monitoring. The cuff structure 12 includes opposing cuff portions 14 and 16 that are dimensioned and configured to sandwich a blood vessel 18 therebetween for blood pressure monitoring. The monitoring cuff structure 12 can be fabricated through a silicone molding technology to have minimal (or very small) restriction on the blood vessel.

In FIGS. 1 and 2, the cuff portion 14 is illustrated as the top portion of the cuff structure 12 and the other cuff portion 16 is illustrated as the bottom portion of the cuff structure (although top and bottom do not imply a necessary relationship during use). The top cuff portion 14 can be formed by a silicone layer. As shown in FIG. 2, a sheet 17 of rigid material, which may be conductive material (e.g., a 75 µm-thick stainless steel sheet), can be embedded within the top cuff portion 14 for shielding environmental effects, such as due to contractions or movements of surrounding tissues. In an embodiment, another sheet of rigid material, similar to the sheet 17, may be placed under the substrate 22 to achieve the same shielding purpose. The elastic sidewalls of the bottom cuff portion 16 (e.g., of Silicone) extend upwardly from a substrate to terminate in a top surface of the bottom cuff portion. As illustrated in FIG. 2, a spacer 19 of a flexible material (e.g., silicone) can be positioned between the top cuff portion 14 and the bottom cuff portion 16, similar to a gasket. The spacer 19 can be dimensioned as to be smaller than the blood vessel 18 diameter to help ensure a proper contact between the cuff structure and the blood vessel, while also controlling the pressure applied to the blood vessel. The cuff structure 12 can be used for mice as well as for other animals, with the size of the structure being determined according to the animal for which the implant is intended to be utilized.

The relative superimposed overlying relationship of the top cuff portion 14 and the bottom cuff portion 16 can be maintained by a retaining mechanism 20, such as a clamp or surgical sutures. In the example of FIG. 2, the retaining mechanism 20 is depicted as a resilient wire clamp (e.g., of stainless steel) that includes an arm that is configured to apply a retaining force that urges the top cuff portion 14 toward the bottom cuff portion 16 and the substrate 22 on which the cuff structure 12 is situated. In other embodiments, the retaining mechanism may be a thin rigid strap, which may be made of metallic material. The retaining strap can be applied to the cuff structure in the same way as the wire clamp shown in FIG. 2, but made to cover all or most of the top surface of the top cuff portion 14 and partial bottom surface of the substrate 22, which coincides with the IC Chip 30. The retaining strap can isolate the environmental variation and tissue growth from being coupled to the MEMS sensor. Those skilled in the art will understand other means (e.g., tabs, latches, clips or the like) that could be utilized for holding the cuff structure in a desired position after the blood vessel has been positioned therein as to extend through a laterally extending aperture in the sidewall of the cuff structure 12.

By way of example, a juncture 26 between top cuff portion 14 and the bottom cuff portion 16 is configured to provide an opening/closing point to provide access to the interior of the cuff 12 for vessel insertion. Such access can be had by removing the retaining clamp 20 and urging the top cuff portion away from the bottom cuff portion 16 and the substrate 22, such as in the direction of arrow 28. For instance, during implantation, a top arm of the clamp 20 is first lifted up and the top cuff portion is also moved in the direction indicated by the arrow 28 to create an opening at the juncture 26. The blood vessel 18 can then be inserted through the opening/closing point at the juncture 26 and the top arm of the clamp can be released to re-engage and secure the cuff structure 12 in position around the blood vessel, such as shown in FIG. 2. It will be appreciated that the cuff structure 12 thus substantially simplifies the implant procedure.

As further shown in FIG. 2, a thin flexible sensing membrane 24, which may be made of silicone or other flexible material, extends across the top edge of the bottom cuff portion 16 to enclose a cavity within the bottom cuff portion. An insulating fluid 29, such as low viscosity oil like fluid (e.g., silicone oil or silicone gel), can occupy the cavity along with a microelectromechanical systems (MEMS) sensor 40. Thus, the MEMS sensor is immersed in the fluid. The MEMS sensor can be implemented as a capacitive pressure sensor or a piezoresistive pressure sensor. The blood vessel 18 is positioned above the MEMS sensor, such as near the center of the cuff structure 12. Thus, the flexible membrane is positioned to interface with the blood vessel to respond to expansion and contraction of said blood vessel. The MEMS sensor is mounted to an integrated circuit (IC) chip 30, which can be mounted to the substrate 22, such as a flexible printed circuit board. The IC chip can constitute a bottom part of the cuff structure 12 from which the sidewalls of the cuff structure extend. The combination of the MEMS sensor and the IC chip on which the MEMS sensor is mounted will be referred to herein as a MEMS/IC pressure sensing module.

In operation, the expansion and contraction of the blood vessel 18 in the cuff structure 12, which is caused by the blood pressure in the blood vessel, will be detected by the MEMS/IC pressure sensing module through the coupling of the insulating fluid in the cavity, which is defined by at least the bottom cuff portion 16 and the sensing membrane 24. Thus, the blood pressure information can be measured by the MEMS/IC pressure sensing module as blood pressure waveform or signal.

By way of example, the fabricated flat cuff structure 12 can be dimensioned and configured to have a miniature form factor, which is sufficiently small for implant in small laboratory animals such as mice. Various dimensions can be implemented according to application requirements. The measured waveform represents a down-scaled version of the blood pressure in the blood vessel 18, which can be calibrated by using a tail-cuff-based blood pressure measurement apparatus. The stainless steel sheet 17 embedded in the top cuff portion 14 further strengthens the structural rigidity of the cuff structure. The stainless steel sheet 17 together with the MEMS/IC pressure sensing module further can effectively suppress environmental variations effect on the cuff performance. The flexible PCB substrate 22 contains discrete components 36 and a radio frequency (RF) powering coil 38. The discrete components 36 and the RF power coil 38 do not necessarily need to be adjacent to the flat cuff structure 12. The discrete components 36 and the RF power coil 38 can be placed away and connected to the cuff structure 12 by flexible wires according to application requirements. The IC chip 30 can be also placed in the middle of the RF powering coil 38 along with other discrete components 36, thus allowing a large IC chip to be employed for the design without enlarging the dimension of the blood pressure measuring device 10, which includes the cuff structure 12, the MEMS sensor 40, and the IC chip 30. A large IC chip can offer an increased sensing capability, including sensing animal body temperature and other bio-potential signals such as electrocardiogram (EKG), electroencephalography (EEG), and electroencephalography (EMG). Circular blood pressure sensing cuff filled by insulating fluid, such as low viscosity oil like fluid (e.g., silicone oil or silicone gel), with an immersed MEMS pressure sensor was shown to be adequate for in vivo blood pressure sensing for large animals, having major arteries size around 1 mm. However, implant experiments showed that circular cuffs failed to work for small animals having small arteries size. The flat blood pressure sensing cuff structure 12 is ideal for small animal in vivo blood pressure monitoring.

Figure 3:
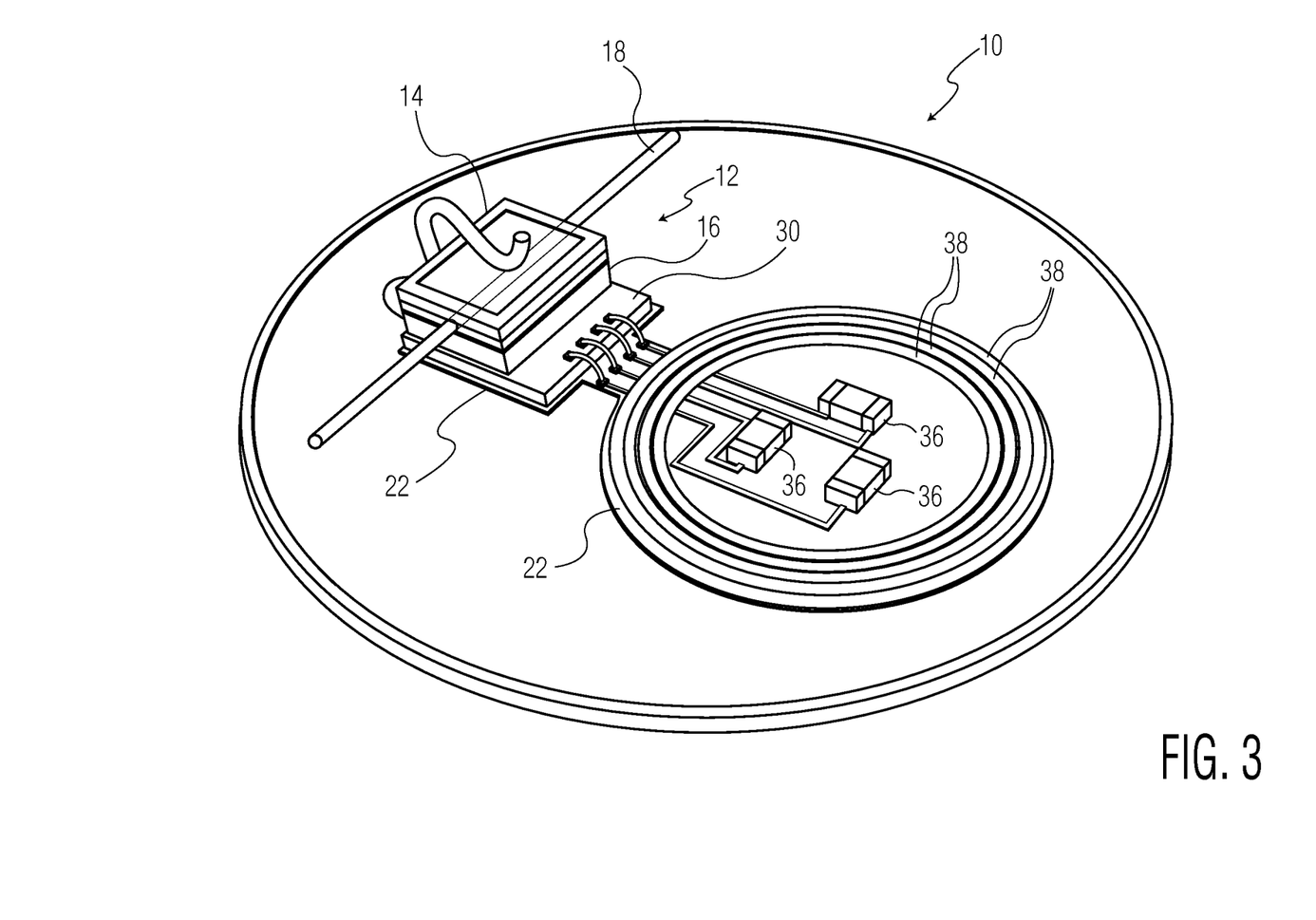
FIG. 3 is a diagram depicting an example embodiment of the implantable blood pressure monitoring device, which is resting on a dime to help demonstrate its small size.

FIG. 3 is a diagram depicting an example embodiment of the implantable blood pressure monitoring device 10. In this example, the device 10 is resting on a dime to help demonstrate its small size.

In view of the foregoing, it will be appreciated that the implantable blood pressure monitoring device 10 thus can be designed to be small, light weight, tissue compatible and easily installable during implantation. Associated circuitry (e.g., as shown and described herein) can further be utilized to measure small fraction of changes of the blood vessel through the fluid 29 coupling to the MEMS pressure sensor 40.

Automatic Off-Set Cancellation Circuitry

Circuitry 100 for performing automatic offset cancellation will be described with respect to examples depicted in FIGS. 4, 5 and 6. Offset adjustment is useful for long term implants as the body environment in which the implant resides may change with the host's health and other conditions. Thus, the circuitry 100 may be used in the implantable blood pressure monitoring device 10. However, the circuitry 100 may be used in other implantable devices or other devices where automatic offset cancellation may be useful.

Figure 4:
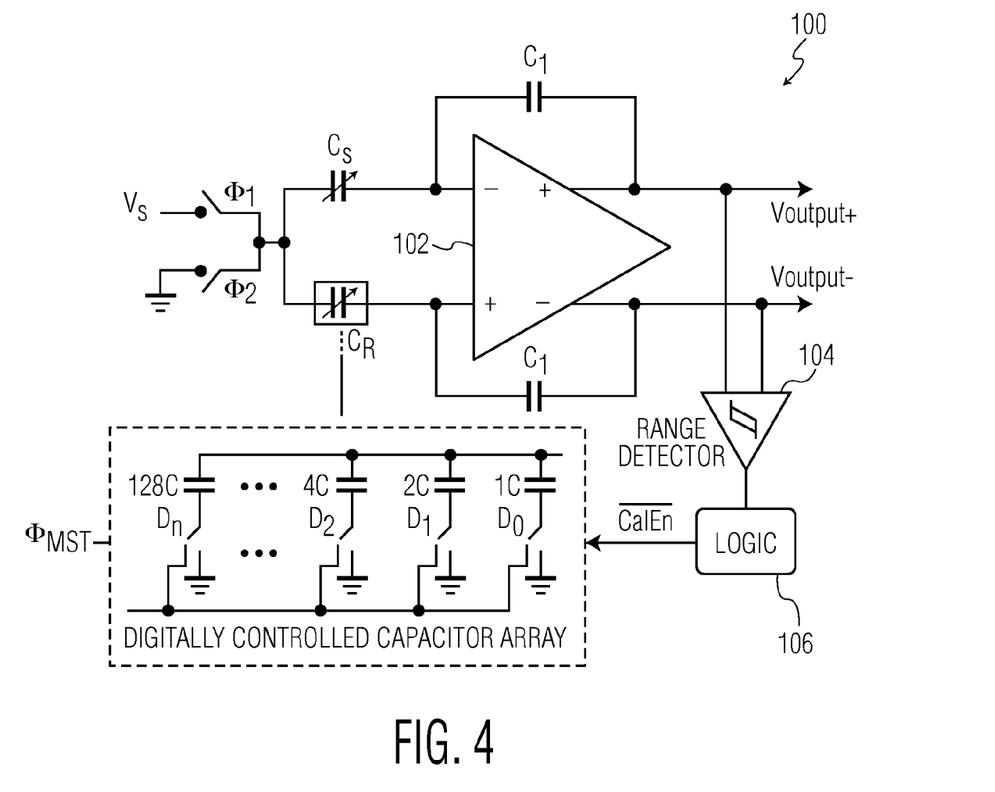
FIG. 4 depicts an example of circuitry that is configured to provide automatic offset cancellation for a sensor, which can be included in the implantable blood pressure monitoring device, in accordance with an embodiment of the invention.
Figure 5:
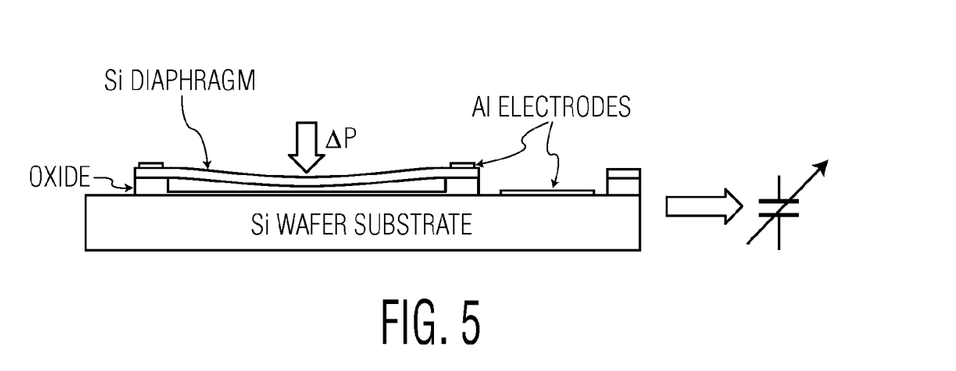
FIG. 5 depicts a single-ended capacitive pressure sensor, which can be included in the implantable blood pressure monitoring device, in accordance with an embodiment of the invention.

FIG. 4 depicts an example of the circuitry 100 that is configured to provide automatic offset cancellation for a sensor in accordance with an embodiment of the invention. A regulated stimulation voltage VS is supplied via a pair of switches based on switch controls signals Φ1 and Φ2 to provide VS to drive respective capacitors Cs and CR. The capacitor CS is connected between the input stimulation voltage VS and an inverting input of an amplifier 102. The capacitor CS has a capacitance that varies as a function of pressure being sensed thereby. For instance, the capacitor CS can be implemented as a capacitive pressure sensor shown and described herein. In one example embodiment, the capacitor CS can be implemented as a single-ended capacitive pressure sensor, such as shown in FIG. 5.

The input signal is also provided to a variable reference capacitor CR coupled between the input stimulation voltage VS and a non-inverting input of the amplifier 102. The capacitor CR can be implemented as a digitally controlled array of capacitors connected in parallel. Each of the capacitors in the array CR is connected between the non-inverting input node and ground or the input stimulation voltage via digitally controlled switches D0-Dn, where n is a positive integer and $2^n$ denotes the number of unit capacitors.

The amplifier 102 is configured to operate as a capacitance-to-voltage converter that provides a differential output at Voutput+ and Voutput−. Feedback capacitors C1 are connected between each input-output pair of the amplifier 102. A range detector 104 is connected to the differential output to provide a range signal to a logic block 106. As an example, the range detector 104 may be a comparator with designed hysteresis characteristics corresponding to the input detection range. The logic block provides an off-set cancellation enable signal (an inverted version thereof) to control calibration of the capacitor array CR. During the initial phase of the circuit operation, the digitally controlled reference capacitor array CR at the amplifier input can be enabled by the logic 106 to cycle through its range of capacitances in response to a switch control signal ΦMST. The logic or other circuitry further can control the cycling through capacitors to find a reference capacitance value that is closely matched to a nominal capacitance of CS. Once the capacitor array CR is within the desired range of the nominal CS, the logic 106 can disable the cycling through the capacitance values.

It will be appreciated that this technique allows a single-ended capacitive pressure sensor with a wide range of nominal capacitance value to be employed, thus greatly simplifying MEMS fabrication process and relaxing tolerance requirements, and also effectively suppressing the output off-set voltage. As one example, the unit capacitor in the capacitor array CR can be set to 20 fF, such as can be implemented as a poly-poly capacitor according to a selected fabrication process (e.g., 1.5 μm CMOS process). Those skilled in the art will appreciate various processes that can be utilized.

Figure 6:
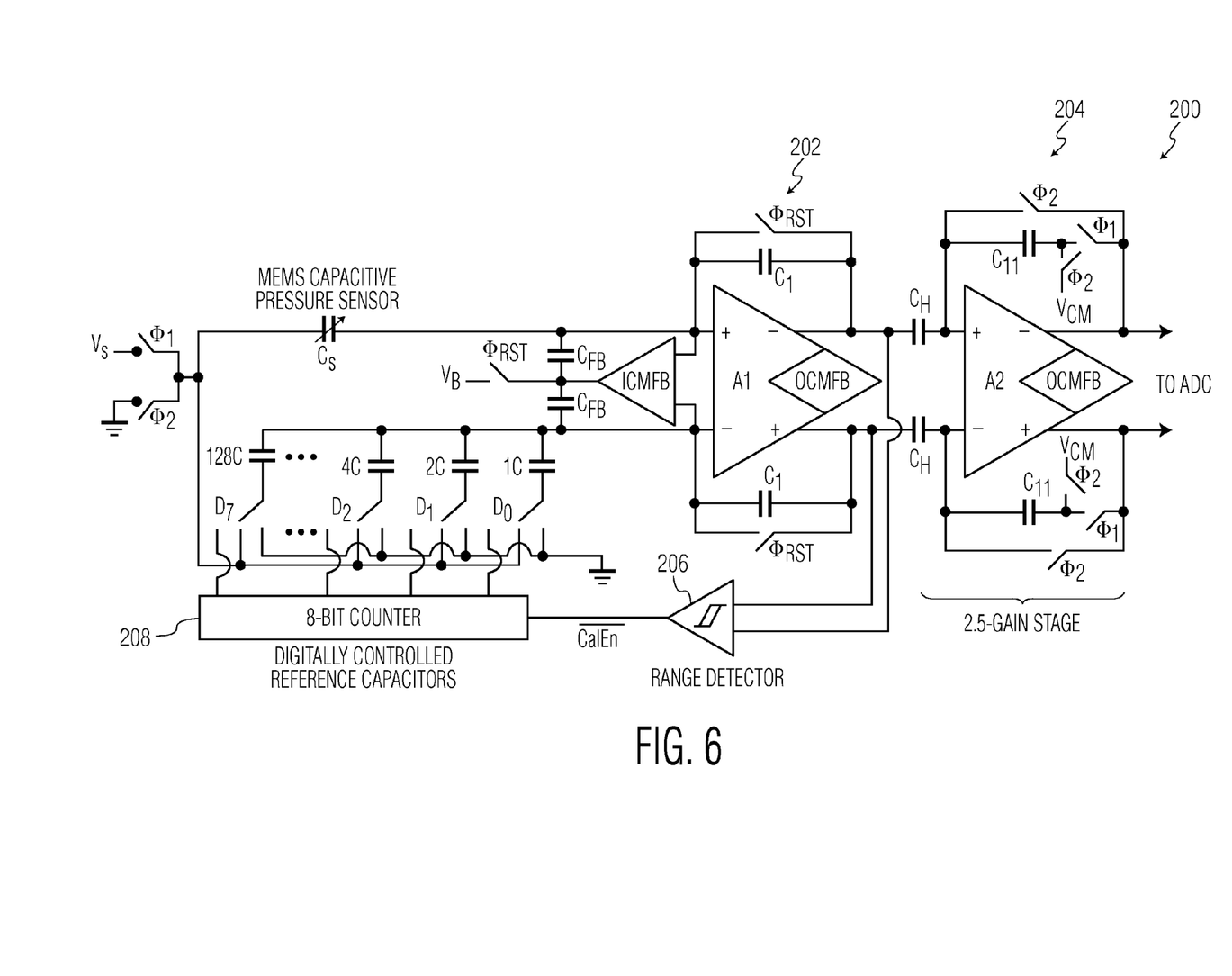
FIG. 6 depicts another example of circuitry that is configured to provide capacitance offset cancellation for a sensor, which can be included in the implantable blood pressure monitoring device, in accordance with an embodiment of the invention.

FIG. 6 depicts another example of circuitry 200 that is configured to provide capacitance offset cancellation for a single-ended capacitive sensor CS (see, e.g., FIG. 5) in accordance with an embodiment of the invention. Similar to the example of FIG. 4, a stimulation voltage VS is supplied to the circuitry 200 by switching a pair of switches, such that the input voltage can alternate between VS and electrical ground based on switch control signals Φ1 and Φ2.

In the example of FIG. 6, the circuitry 200 is implemented as a fully differential correlated-double-sampling (CDS) capacitance-to-voltage (C/V) converter. The input signal is provided to a variable capacitor (e.g., a MEMS capacitive pressure sensor) CS that is connected between the supply input and an inverting input of an amplifier A1. The input signal is also provided to a variable reference capacitor (e.g., digitally controlled reference capacitor array) CR coupled between the input supply and a non-inverting input of the amplifier A1. Input common-mode feedback (ICMFB) can be implemented relative to the input signal at the first stage 202.

Output common-mode feedback (OCMFB) can also be implemented for each of the stages 202 and 204.

The converter 200 includes a multi-stage arrangement of amplifier stages 202 and 204. The first stage 202 operates as a capacitance-to-voltage converter and the second stage 204 is a gain stage configured to amplify the differential output from the first stage for subsequent processing. For instance, the output of the second gain stage 204 can be converted to a corresponding digital signal that can be sent wirelessly to a data acquisition unit, such as shown and described herein.

Feedback capacitors C1 are connected between each input-output pair of the first stage amplifier A1. Switches can also be connected in parallel with each of the capacitors C1 for resetting the first stage in response to a reset signal ΦRST. A range detector 206 is connected to the differential output of the first stage amplifier A1 to provide an off-set cancellation enable signal (an inverted version thereof) to control calibration of the capacitor array CR. For instance, the off-set cancellation enable signal can be provided to enable/disable a counter 208 that controls switches associated with each of the capacitors in the capacitive array CR. For instance, the counter can be an eight-bit counter, although other numbers of bits can be used according to the size of the reference capacitor array CR.

The output of the first stage 202 is provided as the input to the second stage 204 through capacitors CH, which are coupled between the outputs of the first stage and the inputs of the second stage amplifier A2. The second stage also includes feedback capacitors C11 selected to provide a desired amount of gain for the differential input signal. An arrangement of switches is configured to control operation of the second stage 204 for providing the amplified output signal.

By way of example, during the initial phase of the circuit operation, the digitally controlled reference capacitor array CR at the amplifier input can be cycled through its range of capacitances based on an output of the counter 208 to find a reference capacitance value CR that substantially matches a nominal capacitance of the single-ended capacitive sensor CS. Once the capacitor array CR is within the desired range of the single-ended capacitive sensor CS, the range detector 206 disables the counter 208.

The circuitry 200 thus allows the single-ended capacitive pressure sensor CS having a wide range of nominal capacitance value to be employed. As a result, the MEMS fabrication process for the single-ended capacitive sensor CS can be simplified and the tolerance requirements can be relaxed. Additionally, the offset cancellation function effectively suppresses the output offset voltage.

Adaptive RF Powering

In classical RF powering designs, the relative position of the internal coil is usually fixed with respect to the external coil. The case of an implant in an untethered laboratory animal differs from these typical design scenarios in that the inductive coupling factor (k), and thus the power coupled into the implant, can vary drastically over the operating region as the internal coil tilts and changes its position with respect to the stationary external coil. Adaptive RF powering, as described herein, can help prevent power variations from damaging on-chip components or distorting sensitive biosignals and will save the total power of the system. The adaptive RF powering can be used in any mobile powering systems, such as including industrial or medical applications, including the implantable blood pressure monitoring device 10.

The adaptive RF powering will be described with respect to FIGS. 7-10. The adaptive RF powering can be implemented as a closed loop control mechanism that affords a substantially constant received power level.

Figure 7:
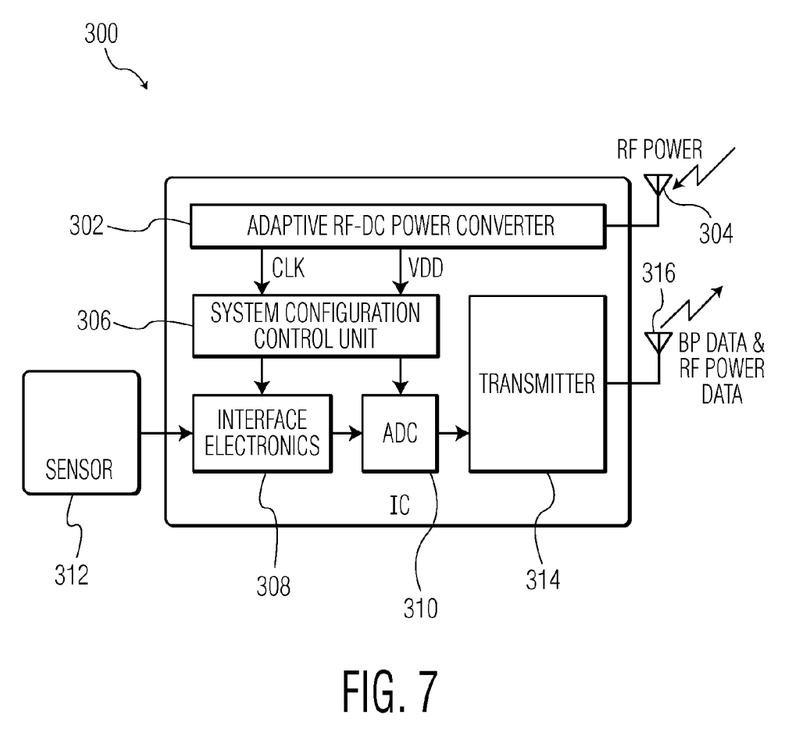
FIG. 7 depicts an example system that can implement adaptive RF powering, which can be included in the implantable blood pressure monitoring device, in accordance with an embodiment of the invention.

FIG. 7 depicts an example system 300 that can implement adaptive RF powering in accordance with an embodiment of the invention. While the example of FIG. 7 demonstrates the adaptive RF powering in the context of an implantable sensor system 300, it will be appreciated that the adaptive RF powering can be implemented in a variety of other contexts, including industrial and medical applications.

In FIG. 7, the system 300 includes an adaptive RF-to-DC converter 302 that receives a wireless RF power signal via an antenna 304. The power signal may also carry additional information (e.g., control instructions) modulated on a carrier. Responsive to the RF power signal, the power converter 302 provides a clock signal (CLK) and a regulated voltage (VDD) to a system configuration control unit 306. The adaptive RF-to-DC power converter 302 is configured to provide sufficient and stable energy to the system 300, such as a system that can be implanted in an untethered animal.

The control unit 306 provides power and control signals to associated circuitry, which in the example of FIG. 7 include interface electronics 308 and an analog-to-digital converter (ADC) 310. A sensor 312 is connected to provide a sensor signal to the interface electronics 308. For example, the sensor can be a capacitive pressure sensor (see, e.g., FIG. 5) and the interface electronics can be implemented to include conversion circuitry, such as shown and described with respect to FIG. 4 or FIG. 6.

The interface electronics 308 thus can provide an analog output signal to the ADC 310. The ADC 310 can convert the analog signal to a corresponding digital signal that is combined with digital control/feedback information from the control unit 306. The combined digital information can be provided to a transmitter (e.g., an FSK transmitter) 314 that wirelessly transmits the signal via an antenna 316. The combined information thus can include sensor data from the sensor 312 and RF power data from the control unit 306. The RF power data can indicate a level of the input RF power received via the antenna 304, such as corresponding to a quantized power level.

The RF power data can be utilized to adaptively adjust the RF power provided by a source of RF power to the system 300. For example, the input voltage for a power amplifier can be adjusted in response to the RF power data so that the received power level at the system 300 remains substantially constant. Thus, the RF power data can provide closed loop feedback for controlling the RF power being delivered to a substantially constant level.

RF powering has been widely used for biomedical implants, where both transmitting and receiving units are properly placed at a fixed distance from each other with a constant RF power coupling coefficient. However, the receiving unit can also be implanted inside a freely moving laboratory animal resulting in a continuously changing RF power coupling. RF powering can also be used to eliminate the need of a battery, thus substantially reducing the overall size and weight of the system 300. Furthermore, a miniature RF coil can be used due to low power budget of the integrated electronics, further minimizing the total system size and weight.

Figure 8:
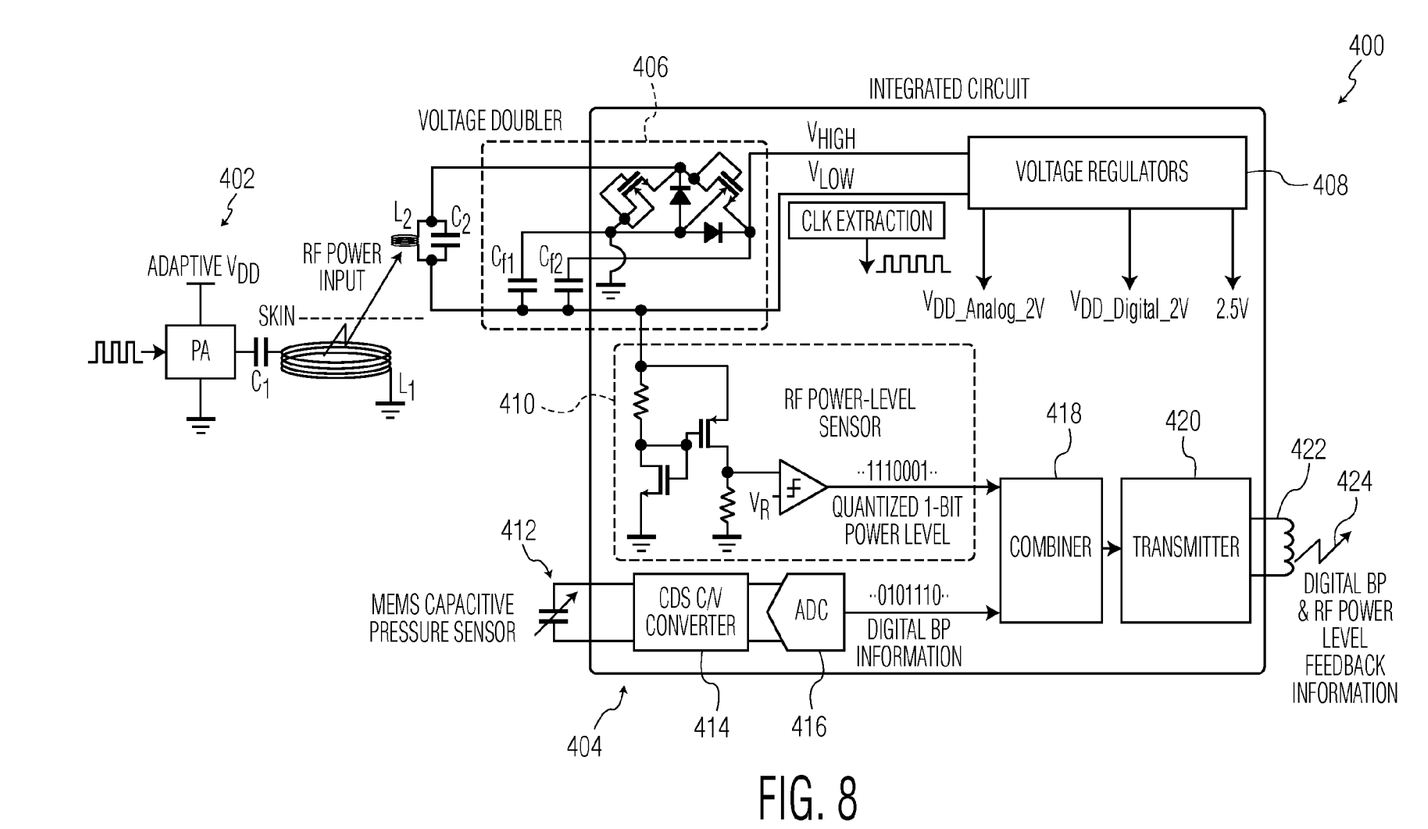
FIG. 8 depicts another example of a system that can implement adaptive RF powering, which can be included in the implantable blood pressure monitoring device, in accordance with an embodiment of the invention.

FIG. 8 depicts another example of a system 400 that can implement adaptive RF powering in accordance with an embodiment of the invention. The system 400 demonstrates a remote power source 402 that is configured to provide RF power to a moveable apparatus 404, such as an implant within an untethered animal. The power source 402 can be implemented as a power amplifier (e.g., a class-E amplifier) that provides an output signal to a coil L1 that is configured to provide RF powering. For the example of a class-E power amplifier, the output power varies based on an input supply voltage VDD and a duty cycle of a switching signal. Given a constant duty cycle, the power source 402 controls the output power as a function of the input supply voltage VDD. Thus, in the system 400, circuitry is provided to adjust VDD (e.g., discretely or continuously) in response to RF power data provided by the moveable apparatus 404. A capacitor C1 can be connected between the amplifier and the coil L1 to provide the desired alternating power signal to the coil L1.

The RF power signal can be received at the apparatus 404 via a coil antenna L2. The inductive coupling results in current that is converted to a voltage by power conversion circuitry 406, such as a voltage doubler. The conversion circuitry 406 can thus provide a differential voltage, indicated at VHIGH and VLOW, to an arrangement of voltage regulation circuitry 408. The voltage regulation circuitry 408 can in turn provide regulated output voltage at or near corresponding levels needed for operation of the associated circuitry according to the received RF power.

An RF power level sensor 410 provides a digital signal indicative of the received RF power level. In the example of FIG. 8, the RF power level sensor 410 can be coupled to monitor the VLOW voltage provided by the conversion circuitry 406. The sensed voltage is mirrored through an arrangement of transistors to provide a corresponding voltage across a sense resistor. The voltage is provided to an input of a comparator (or threshold detector), which compares the voltage to a reference voltage (VR). The comparator in turn provides a digital output signal as a quantized one-bit signal representing the power level of the RF input power relative to the reference voltage VR. For example, the quantized power signal can be generated continuously while the apparatus 404 receives RF powering from the source 402.

An input supply voltage from the regulator 408 is provided to power a variable capacitor (e.g., a MEMS capacitor pressure sensor) 412. A capacitance-to-voltage converter and sampling circuitry 414 converts the capacitance to a corresponding analog voltage signal. The converter and sampling circuitry can be implemented as shown and described with respect to FIGS. 4 and 6, such as to provide for automatic offset cancellation. An ADC 416 converts the analog voltage signal to a corresponding digital signal that represents the sensor signal. Thus, for the example of blood pressure monitoring, the ADC provides a digital signal indicative of the sensed blood pressure.

A combiner 418 combines the digital outputs from the power sensor 410 and the ADC 416. For instance, the combiner 418 can be implemented as a two-channel combiner and parity generator that combines the respective signals for transmission as a digital signal via a transmitter 420. The transmitter 420 can be a frequency-shift keyed transmitter that generates a wireless signal 424 via an antenna 422, although other types of transmitters could be used. Thus, the wireless digital signal 424 contains both sensor information as well as the RF power feedback information. The wireless signal 424 can be received at an external receiver and used to adjust the power level at the external source 402.

Figure 9:
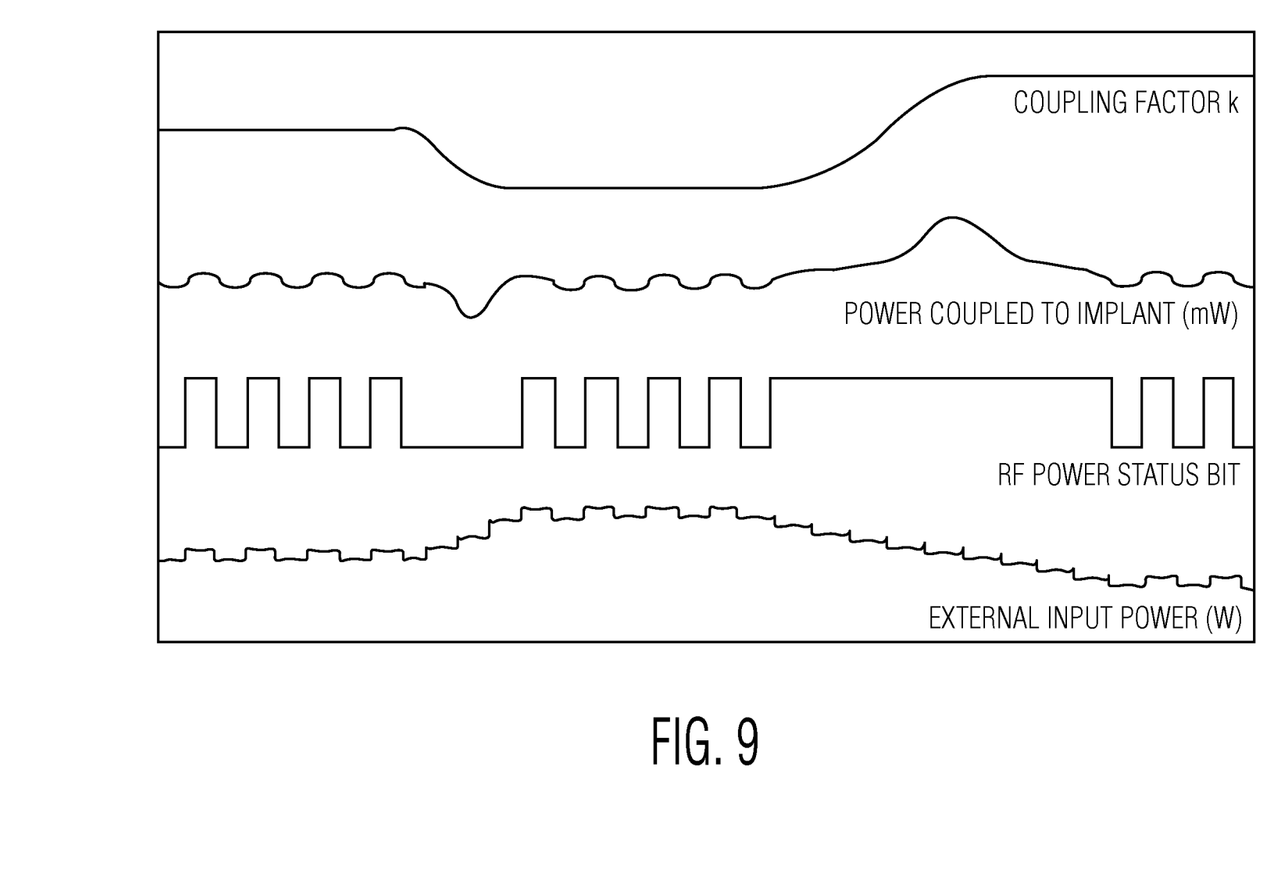
FIG. 9 is a timing diagram illustrating the operation of the system shown in FIG. 8 in accordance with an embodiment of the invention.

FIG. 9 is a timing diagram illustrating the operation of the adaptive power control system in the context of the system 400 of FIG. 8. In the example of FIG. 9, a coupling factor k is plotted with respect to time along with signals representing power coupled to the implant, the power level signal (e.g., from the power sensor 410), and the external input power. As mentioned above, the external input power is adjusted as a function of the power sensing data, as represented by the RF power feedback information in the signal 424.

As illustrated in FIG. 9, when k decreases, the power coupled to the implant temporarily drops, causing the power data bit to remain low. The adaptive controlling program (e.g., implemented in the external RF powering system) steps up the external input power to regain the coupled power in the implant system to a desired level. In this example, the transmitting RF power can be controlled by adjusting a supply voltage of a class-E amplifier (PA) implemented as the external power source 402. Thus, when k increases, the external input power is stepped down to a proper level resulting in lower external power consumption, thus a reduced RF input power. When k is constant (e.g., moveable system or implant not moving), the power data bit alternates between a high and low states, causing a steady power with ripple at the step up/down frequency.

Figure 10:
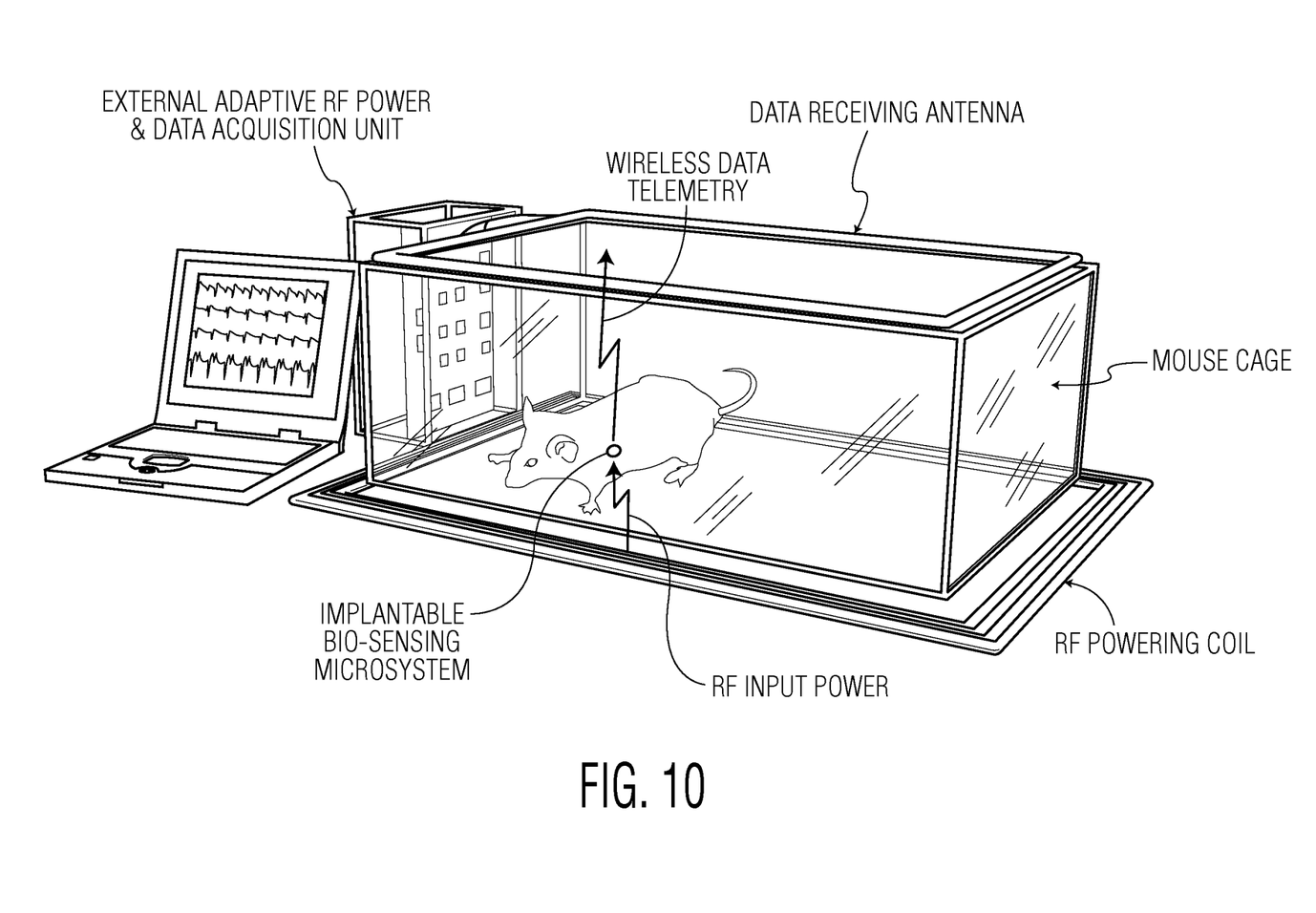
FIG. 10 depicts an example of a blood pressure monitoring system implanted in an animal in accordance with an embodiment of the invention.

FIG. 10 depicts an example of a blood pressure monitoring system implanted in an animal in accordance with an embodiment of the invention. The system implanted can be configured according to one or any combination of features shown and described herein.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An implantable flat blood pressure sensing cuff structure comprising:
a first portion that comprises a sidewall that extends from a surface and contains a pressure sensor;
a second portion that is configured to overlie and be removable relative to the first portion, the first and second portions being configured to provide an aperture extending transversely through the cuff structure for receiving a blood vessel therein generally sandwiched between the first portion and the second portion when the second portion is positioned on the first portion such that the pressure sensor is operative to detect vessel expansion and contraction, wherein a layer of rigid material is disposed within the second portion and in overlying relation relative to the pressure sensor to isolate environmental variation from being coupled to the pressure sensor; and
a flexible membrane that retains a fluid within the sidewall of the first portion, the flexible membrane being positioned to interface with the blood vessel to respond to expansion and contraction of said blood vessel that provides blood pressure information, the flexible membrane being configured to conform to the shape of the blood vessel without flattening the blood vessel when interfaced with the blood vessel, the expansion and contraction of the blood vessel being detected by the pressure sensor through coupling of the fluid within the sidewall of the first portion so that a down-scaled version of the blood pressure in the blood vessel is measured by the pressure sensor.

2. The cuff structure of claim 1, wherein the pressure sensor comprises a capacitive pressure sensor located inside the fluid between the flexible membrane and a substrate on which the first portion is situated.

3. The cuff structure of claim 1, wherein the pressure sensor comprises a piezoresistive pressure sensor located inside the fluid between the flexible membrane and a substrate on which the first portion is situated.

4. The cuff structure of claim 1, wherein the pressure sensor is coupled to a circuit board that comprises an integrated circuit chip.

5. The cuff structure of claim 4, wherein the pressure sensor is mounted on the integrated circuit chip, which is mounted on the circuit board.

6. The cuff structure of claim 5, wherein the integrated circuit chip is mounted on the circuit board in the middle of an RF powering coil mounted on the circuit board.

7. The cuff structure of claim 1, further comprising a retaining mechanism for retaining the relative position between the first portion and the second portion.

8. The cuff structure of claim 7, wherein the retaining mechanism is a rigid strap that covers at least some of a top surface of the second portion and at least a bottom surface of a substrate coupled to the first portion.

9. The structure of claim 1, wherein the pressure sensor is positioned in a cavity filled with the fluid such that the pressure sensor is immersed in the fluid.

10. An implantable blood pressure monitoring device comprising:
    a substrate; and
    a flat blood pressure sensing cuff structure situated on the substrate, the cuff structure comprising;
        a first portion that comprises a sidewall that extends from a surface and contains a pressure sensor;
        a second portion that is configured to overlie and be removable relative to the first portion, the first and second portions being configured to provide an aperture extending transversely through the cuff structure for receiving a blood vessel therein generally sandwiched between the first portion and the second portion when the second portion is positioned on the first portion such that the pressure sensor is operative to detect vessel expansion and contraction; and
        a flexible membrane that retains a fluid within the sidewall of the first portion, the flexible membrane being positioned to interface with the blood vessel to respond to expansion and contraction of said blood vessel that provides blood pressure information, the flexible membrane being configured to conform to the shape of the blood vessel without flattening the blood vessel when interfaced with the blood vessel, the expansion and contraction of the blood vessel being detected by the pressure sensor through coupling of the fluid within the sidewall of the first portion so that a down-scaled version of the blood pressure in the blood vessel is measured by the pressure sensor,
        wherein the cuff structure further comprises a layer of rigid material disposed within the second portion and in overlying relation relative to the pressure sensor to isolate environmental variation from being coupled to the pressure sensor.

11. The device of claim 10, wherein the pressure sensor comprises a capacitive pressure sensor located inside the fluid between the flexible membrane and a substrate on which the first portion is situated.

12. The device of 10, wherein the pressure sensor comprises a piezoresistive pressure sensor located inside the fluid between the flexible membrane and a substrate on which the first portion is situated.

13. The device of claim 10, wherein the substrate includes a circuit board that comprises an integrated circuit chip and wherein the pressure sensor is coupled to the circuit board.

14. The device of claim 13, wherein the pressure sensor is mounted on the integrated circuit chip, which is mounted on the circuit board.

15. The device of claim 13, further comprising:
    an RF powering coil mounted to the circuit board for receiving a wireless RF powering signal from a remote RF power source;
    circuitry configured to convert the RF powering signal for powering the integrated circuit chip and the pressure sensor; and
    an antenna for wirelessly transmitting sensor information from the pressure sensor to a receiver.

16. The device of claim 15, wherein the pressure sensor is mounted on the circuit board, and wherein the integrated circuit chip is mounted on the circuit board within in the RF powering coil.

17. The device of claim 10, wherein the cuff structure further comprises a retaining mechanism for retaining the relative position between the first portion and the second portion.

18. The device of claim 10, wherein the pressure sensor is positioned in a cavity filled with the fluid such that the pressure sensor is immersed in the fluid.

19. An implantable flat blood pressure sensing cuff structure comprising:
    a first portion that comprises a sidewall that extends from a surface and contains a pressure sensor; and
    a second portion that is configured to overlie and be removable relative to the first portion, the first and second portions being configured to provide an aperture extending transversely through the cuff structure for receiving a blood vessel therein generally sandwiched between the first portion and the second portion when the second portion is positioned on the first portion such that the pressure sensor is operative to detect vessel expansion and contraction,
    wherein a layer of rigid material is disposed within the second portion and in overlying relation relative to the pressure sensor to isolate environmental variation from being coupled to the pressure sensor.

20. An implantable blood pressure monitoring device comprising:
    a substrate; and
    a flat blood pressure sensing cuff structure situated on the substrate, the cuff structure comprising;
        a first portion that comprises a sidewall that extends from a surface and contains a pressure sensor; and
        a second portion that is configured to overlie and be removable relative to the first portion, the first and second portions being configured to provide an aperture extending transversely through the cuff structure for receiving a blood vessel therein generally sandwiched between the first portion and the second portion when the second portion is positioned on the first portion such that the pressure sensor is operative to detect vessel expansion and contraction,
        wherein a layer of rigid material is disposed within the second portion and in overlying relation relative to the pressure sensor to isolate environmental variation from being coupled to the pressure sensor.

* * * * *